(12) United States Patent
Yarger et al.

(10) Patent No.: US 7,834,891 B2
(45) Date of Patent: Nov. 16, 2010

(54) SYSTEM AND METHOD FOR PERSPECTIVE-BASED PROCEDURE ANALYSIS

(75) Inventors: Richard W. Yarger, Berkeley, IL (US); Mark Morita, Arlington Heights, IL (US); Steven L. Fors, Chicago, IL (US); Vijayanand Tirumalai, Kenosha, WI (US)

(73) Assignee: General Electric Company, Schenectady, NY (US)

( * ) Notice: Subject to any disclaimer, the term of this patent is extended or adjusted under 35 U.S.C. 154(b) by 1420 days.

(21) Appl. No.: 10/996,631

(22) Filed: Nov. 23, 2004

(65) Prior Publication Data

US 2006/0111937 A1 May 25, 2006

(51) Int. Cl.
*G09G 5/00* (2006.01)
(52) U.S. Cl. ...................................... 345/619
(58) Field of Classification Search .................. 345/619
See application file for complete search history.

(56) References Cited

U.S. PATENT DOCUMENTS 6,574,629 B1 * 6/2003 Cooke et al. .................. 707/10

2004/0068423 A1 * 4/2004 Shaw ........................... 705/3

* cited by examiner

*Primary Examiner*—Xiao M Wu
*Assistant Examiner*—Maurice McDowell, Jr.
(74) *Attorney, Agent, or Firm*—Hanley, Flight & Zimmerman, LLC (57) ABSTRACT

Certain embodiments of the present invention provide a method and system for using medical perspectives to improve medical workflow. Certain embodiments of a system for using medical perspectives for improved screening analysis include a picture archiving and communication system (PACS) workstation capable of being used for reviewing images and at least one display capable of displaying images for review. The system also includes a default perspective including a first plurality of images organized according to a default criterion, wherein the default perspective is used to review the first plurality of images via the PACS workstation. The system includes one or more additional perspectives organizing image sets according to certain criteria. A user may select one or more of the additional perspectives for reviewing image sets or subsets via the PACS workstation. The system may also include tools and reporting templates for use with images within the perspectives.

21 Claims, 4 Drawing Sheets

An example of the "All Images" Perspective on a 2 monitor display

An example of the "CC Only" Perspective on a 2 monitor display

An example of the "MLO Only" Perspective on a 2 monitor display

SYSTEM AND METHOD FOR PERSPECTIVE-BASED PROCEDURE ANALYSIS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to perspectives in a healthcare environment. In particular, the present invention relates to use of medical perspectives to improve medical image reading and workflow.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility. Data entry and access is also complicated in a typical healthcare facility.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools.

Current systems use general techniques known as "hanging protocols" to format display of images, such as mammogram images. Hanging protocols present a single perspective or view to a user, such as a radiologist. Images may be grouped according to simple, non-procedure specific characteristics such as DICOM series or series number. Single perspectives typically provide all available images for a patient and/or study. Single perspectives are too general and often create additional work for a radiologist or other reviewer. Single perspectives are currently created based on general characteristics of a single instance of a procedure. However, the procedure characteristics may have different values for other instances of a procedure. Thus, a user, such as a radiologist, is often forced to manually format images upon display or create a new protocol altogether. Creation of a new protocol is often a time-consuming, manual task. Additionally, manual sorting or hanging of images is a time-consuming task. Therefore, a system and method for improved sorting and display of images for review would be highly desirable.

Thus, there is a need for a system and method to improve workflow and productivity using medical perspectives to improve image reading and medical workflow.

BRIEF SUMMARY OF THE INVENTION

Certain embodiments of the present invention provide a method and system for using medical perspectives to improve medical workflow. Certain embodiments of a system for using medical perspectives for improved screening analysis include a picture archiving and communication system (PACS) workstation capable of being used for reviewing images and at least one display capable of displaying images for review. The system also includes a default perspective including a first plurality of images organized according to a default criterion, wherein the default perspective is used to review the first plurality of images via the PACS workstation. Additionally, the system includes a second perspective including a second plurality of images organized according to a second criterion, wherein the second perspective is selectable by a user for reviewing the second plurality of images via the PACS workstation. The system may include a plurality of perspectives.

In an embodiment, the second plurality of images is a subset of the first plurality of images. The default criterion may allow display of all available images, for example. The second criterion may include image attributes, such as procedure-specific image attributes. In an embodiment, the second perspective includes a layout of the second plurality of images based on the image attributes.

In an embodiment, the system further includes at least one tool for navigation and/or manipulation of images, for example. The tool(s) may allow a user to navigate and/or manipulate one or more of the images in a synchronous manner within a perspective. The system may also include a template for recording findings for report generation. The template may include a plurality of screening results selectable by a user, for example.

Certain embodiments of a method for providing medical perspectives for improved screening analysis include providing a default perspective for reviewing images on a PACS workstation, wherein the default perspective includes a first plurality of images organized according to a default criterion, and allowing a user to select a second perspective for reviewing images on the PACS workstations, wherein the second perspective includes a second plurality of images organized according to a second criterion. The default criterion may allow display of all available images, for example. The second criterion may include image attributes, such as procedure-specific image attributes, for example.

In an embodiment, the method further includes navigating and/or manipulating image(s) in the first and/or second plurality of images. Navigation and/or manipulation may include navigating and/or manipulating one or more of the images in a synchronous manner within a perspective, for example. In an embodiment, the method includes generating a report using a plurality of screening results selectable by a user.

Certain embodiments of a system for image analysis using perspectives include a default perspective including a first plurality of images organized according to a default criterion, and a second perspective including a second plurality of images organized according to a second criterion. The default perspective is used to review the first plurality of images via a PACS workstation. The second perspective is selectable by a user for reviewing the second plurality of images via the PACS workstation. The second plurality of images is a subset of the first plurality of images, for example. The second criterion comprises image attributes, for example.

Certain embodiments of a computer-readable storage medium having a set of instructions for a computer include a perspectives management routine for coordinating a plurality of perspectives including images, and a processing routine for processing images in the perspectives according to at least one of display functions, editing functions, and transmission functions, for example. The perspectives management routine allows a user to switch between perspectives to view different image layouts, for example. The set of instructions may further include a reporting routine for generating a report based on a template including analysis results relating to the perspectives. The set of instructions may also include a perspective creation routine for creating at least one perspective based on imaging-specific attributes.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
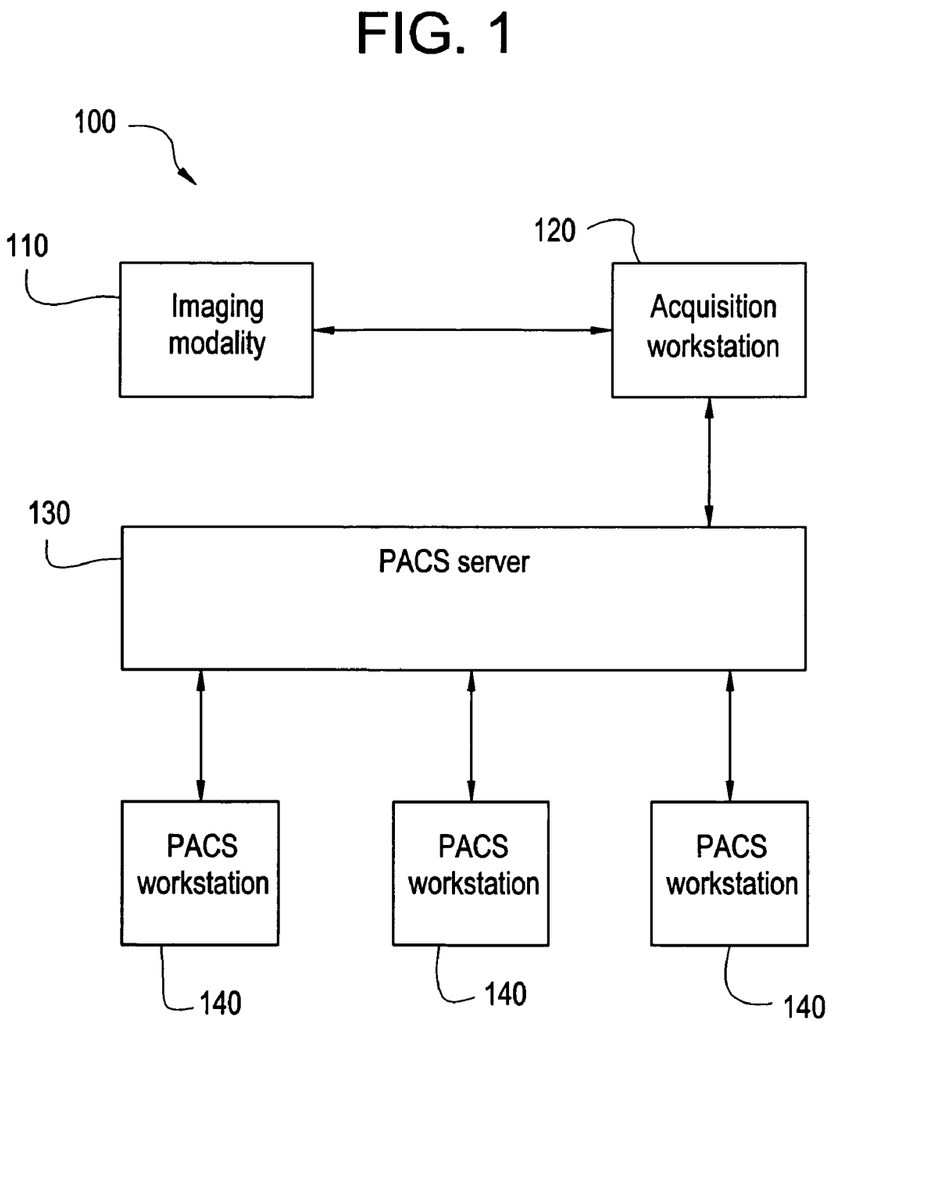
FIG. 1 illustrates an exemplary picture archiving and communication system used in accordance with an embodiment of the present invention.

FIG. 1 illustrates an exemplary Picture Archiving and Communication System (PACS) 100 used in accordance with an embodiment of the present invention. The PACS system 100 includes an imaging modality 110, an acquisition workstation 120, a PACS server 130, and one or more PACS workstations 140. The system 100 may include any number of imaging modalities 110, acquisition workstations 120, PACS servers 130 and PACS workstations 140 and is not in any way limited to the embodiment of system 100 illustrated in FIG. 1. The components of the system 100 may communicate via wired and/or wireless communication, for example, and may be separate systems and/or integrated to varying degrees, for example.

In operation, the imaging modality 110 obtains one or more images of a patient anatomy. The imaging modality 110 may include any device capable of capturing an image of a patient anatomy such as a medical diagnostic imaging device. For example, the imaging modality 110 may include an X-ray imager, ultrasound scanner, magnetic resonance imager, or the like. Image data representative of the image(s) is communicated between the imaging modality 110 and the acquisition workstation 120. The image data may be communicated electronically over a wired or wireless connection, for example.

In an embodiment, the acquisition workstation 120 may apply one or more preprocessing functions, for example, to the image data in order to prepare the image for viewing on a PACS workstation 140. For example, the acquisition workstation 120 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions differ from processing functions applied to image data in that the processing functions are not modality specific and are instead applied at the end of the imaging and display workflow (for example, at a display workstation 140).

The image data may then be communicated between the acquisition workstation 120 and the PACS server 130. The image data may be communicated electronically over a wired or wireless connection, for example.

The PACS server 130 may include computer-readable storage media suitable for storing the image data for later retrieval and viewing at a PACS workstation 140. The PACS server 130 may also include one or more software applications for additional processing and/or preprocessing of the image data by one or more PACS workstations 140.

One or more PACS workstations 140 are capable of or configured to communicate with the server 130. The PACS workstations 140 may include a general purpose processing circuit, a PACS server 130 interface, a software memory, and/or an image display monitor, for example. The PACS server 130 interface may be implemented as a network card connecting to a TCP/IP based network, but may also be implemented as a parallel port interface, for example.

The PACS workstations 140 may retrieve or receive image data from the server 130 for display to one or more users. For example, a PACS workstation 140 may retrieve or receive image data representative of a computed radiography ("CR") image of a patient's chest. A radiologist or user may then examine the image for any objects of interest, such as tumors, lesions, etc., for example.

The PACS workstations 140 may also be capable of or configured to apply processing functions to image data. For example, a user may desire to apply processing functions to enhance features within an image representative of the image data. Processing functions may therefore adjust an image of a patient anatomy in order to ease a user's diagnosis of the image. Such processing functions may include any software-based application that may alter a visual appearance or representation of image data. For example, a processing function can include any one or more of flipping an image, zooming in an image, panning across an image, altering a window and/or level in a grayscale representation of the image data, and altering a contrast and/or brightness an image.

In an embodiment, the PACS system 100 may provide one or more perspectives for viewing images and/or accessing applications at a PACS workstation 140. Perspectives may be provided locally at the PACS workstation 140 and/or remotely from the PACS server 130. In an embodiment, the PACS system 100 includes a perspectives manager capable of being used for reviewing images via a plurality of perspectives. The PACS server 130 and/or a PACS workstation 140 may include the perspectives manager, or the perspectives manager may be implemented in a separate system. In an embodiment, each PACS workstation 140 may include a perspectives manager.

In operation, for example, a user, such as a radiologist, selects a set of images, such as screening mammogram images, chest screening images and/or other computed radiography (CR), digital radiography (DR), and/or digital x-ray (DX) screening images, to review at a PACS workstation 140. The images are displayed in a default perspective, such as the default perspective shown in FIG. 2. In an embodiment, the default perspective includes all available images in the set. The radiologist may read all views of a patient's breasts from the default perspective, for example. Although the default perspective layout may be crowded, the default perspective allows a user an overall view of a screening. The view from the default perspective allows a user, such as a radiologist, to quickly determine which additional perspective(s) to view.

After viewing the image(s) from a high level, the user may then switch to another perspective. For example, a radiologist switches to a Cranio-Caudal (CC) perspective, such as the CC perspective shown in the middle section of FIG. 2. Switching to the CC perspective displays CC images of a breast and filters out other images, for example. The CC perspective layout places right CC and left CC images in optimal areas of the perspective layout. Additionally, existing historical CC images from previous screening mammograms may be loaded and displayed. Right and left historical CC images may be displayed in positions relative to the other right and left CC images, for example.

Figure 2:
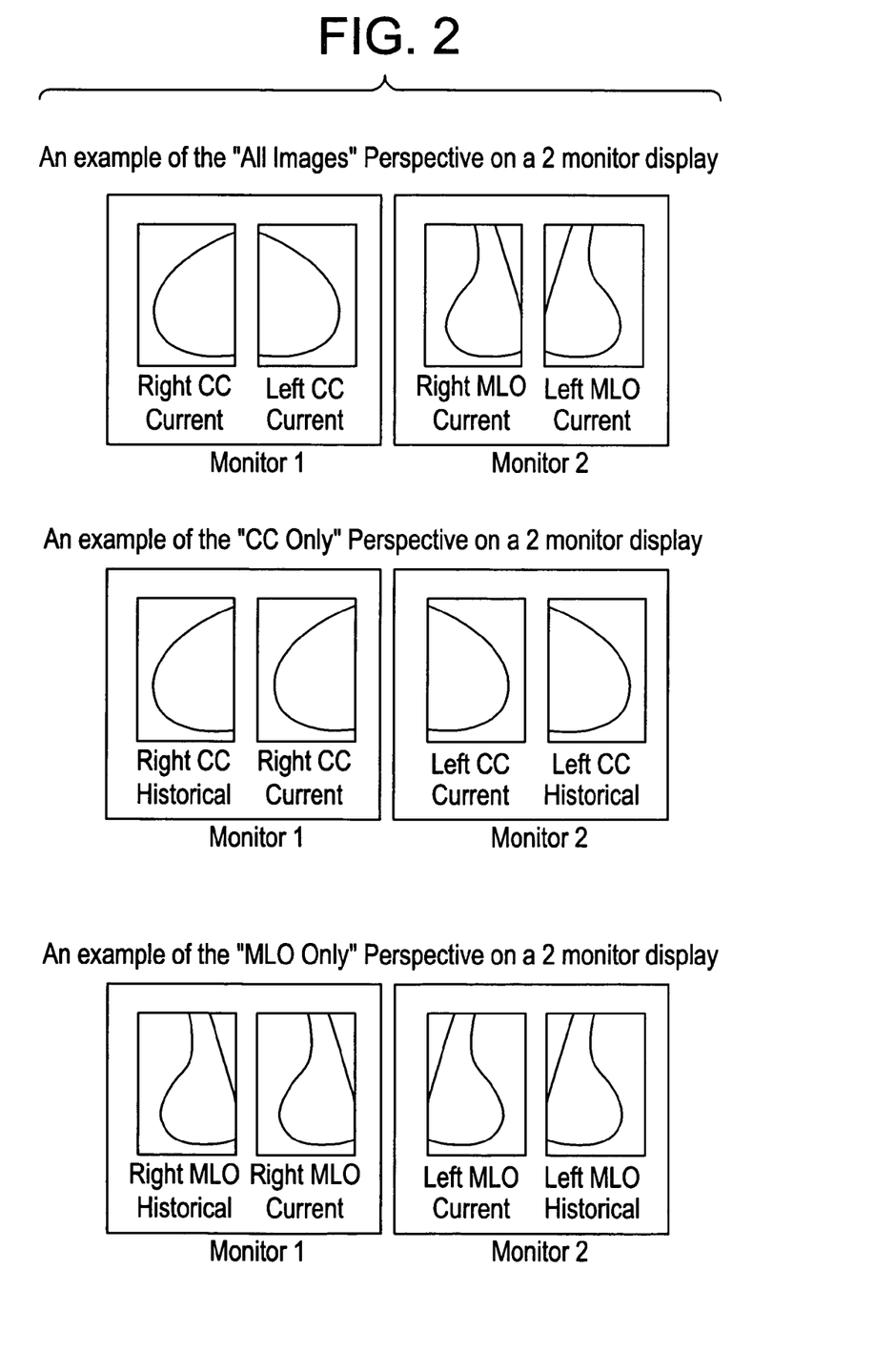
FIG. 2 depicts an example of a plurality of perspectives arranged in accordance with an embodiment of the present invention.

After analyzing the CC images in the CC perspective, the radiologist may then switch to a Medio-Lateral Oblique (MLO) perspective, for example, such as the MLO perspective shown at the bottom of FIG. 2. Switching to the MLO perspective displays MLO images. The MLO perspective layout places right and left MLO images in optimal areas of the perspective layout, for example. Existing historical MLO images from pervious screening mammograms may also be loaded and displayed, for example. Right and left historical MLO images may be displayed in positions relative to the other right and left MLO images, for example.

In an embodiment, images in each perspective are matched to areas of the perspective layout based on image information. For example, images may be organized in a perspective layout based on protocol-specific image attributes, such as mammogram specific image attributes found in image headers (e.g., DICOM headers). Thus, perspective may be reproduced for each instance of a procedure.

Within each perspective, tools may be provided to navigate and/or manipulate images. In an embodiment, the tools may navigate and/or manipulate images in a synchronous manner. For example, when a tool is applied to a left breast image, changes may to the left breast image are also applied to the corresponding right breast image (and vice versa). Tools may include window, width, window level, inversion, zoom, and/or other processing tools, for example. In an embodiment, when a tool is applied to one image, a mirror effect of the tool is applied to the corresponding image(s). For example, when a directional tool is applied to a left breast image, the same directional tool is applied to a right breast image in a mirrored fashion (and vice versa). Directional tools may include pan, spatial cursor, and/or other direction tools, for example.

Upon completion of an image analysis, a user is provided with a reporting mechanism to record findings. For example, the user may be provided with a template-based reporting mechanism that allows the user to record findings quickly without having to type full text. Screening results, such as screening mammogram or chest screening results, may be summarized in one or more templates allowing a user to choose an applicable template and/or result. For example, a template may include a pull-down list of options and/or standardized terminology (e.g., BI-RADS or Breast Image-Reporting and Data System categories) to fill in template fields. The report may then be documented and stored and/or transmitted to a physician or other healthcare personnel, for example. In an embodiment, reporting may be connected to a HIS, RIS, CIS, PACS, and/or other information system, for example.

One or more perspectives may be modified and/or saved for a user or group of users, for example. Perspective(s) may also be modified and/or saved for a procedure or category of procedures, for example, such as screening, bilateral exam, etc. Different protocol(s), script(s), etc. may be included in a perspective in addition to images, for example. Perspective(s) may include current and historical information, such as images, laboratory results, patient data, and/or other information, from one or more modalities, for example.

Figure 3:
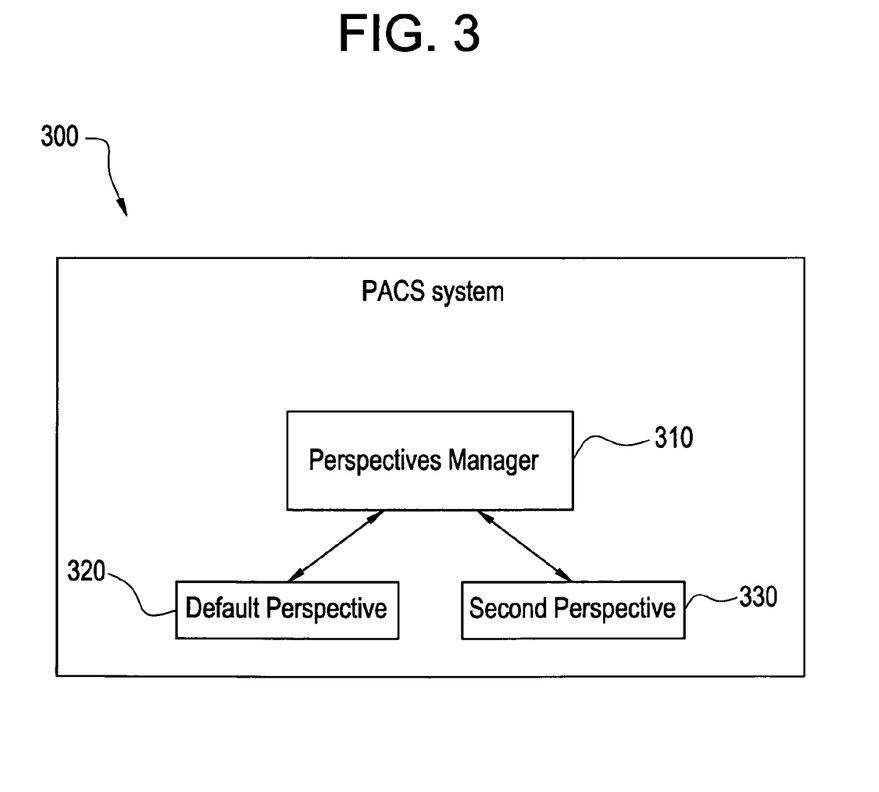
FIG. 3 illustrates a PACS system including a perspectives manager used in accordance with an embodiment of the present invention.

FIG. 3 illustrates a PACS system 300 including a perspectives manager used in accordance with an embodiment of the present invention. The system 300 includes a perspectives manager 310, a default perspective 320, and a second perspective 330. The system 300 may include a plurality of perspectives 330 in addition to the default perspective 300. For purposes of illustration only, the system 300 is described with a default perspective 320 and second perspective 330. The components of the system 300 may be implemented in software and/or in hardware, for example. The components of the system 300 may be integrated and/or implemented separately, for example. In an embodiment, the system 300 is a PACS workstation, such as the PACS workstation 140.

In an embodiment, the perspectives 320, 330 are software components that save visual component positioning and interactions between images and/or applications based on workflow. Medical perspectives 320, 330 may be used to create a plurality of benefits for users of the system 300. For example, perspectives 320, 330 may provide patient context sharing between different image(s) and/or application(s) that a user views. Additionally, for example, perspectives 320, 330 provide an ability to easily switch between different configurations or perspectives 320, 330 based on which images and/or applications a user wishes to view at any given point. Furthermore, for example, perspectives 320, 330 provide an ability to store or "remember" specific workflow steps. Perspectives 320, 330 provide a mechanism to save and display information relevant to a particular user, group, and/or function, for example.

The medical application perspectives manager 310 may be an integrated or standalone software and/or hardware unit for coordinating and controlling one or more perspectives 320, 330. Users of the system 300 may "switch to" or "be assigned" a medical perspective 320, 330 via the medical application perspectives manager 310. In an embodiment, a user initially views the default perspective 320. Based on the available perspectives 320, 330, a user may toggle between the perspectives 320, 330 to review image(s), exam results, and/or other data, for example. A user may toggle between available perspectives 320, 330 via the medical application perspectives manager 310 using a mousing device, keyboard shortcuts, gaze tracking, and/or voice command, for example. In an embodiment, the perspectives manager 310 may include a database or other memory to store perspectives 320, 330 and related information. For example, specific workflows of individual radiologists and/or cardiologists may be stored in the database so that each radiologists/cardiologists uses the same workflow through the same sequence of perspectives wherever the user logs in to the system 300. Thus, a user has the advantage of reading exams and other data quickly and efficiently on any diagnostic workstation, for example.

In an embodiment, the medical perspective manager 310 includes and/or communicates with an authentication unit. The authentication unit may include software and/or hardware to verify a user's right to access one or more of the manager 310, perspectives 320, 330, and/or other data, for example. In an embodiment, authentication via the perspectives manager 310 allows access to relevant perspectives 320, 330, and other data for a user. For example, if a user logs on to a system running the perspectives manager 310, based on previous saving of a default perspective, the user is automatically shown a series of AP and lateral chest images.

In operation, a user, such as a radiologist or cardiologist, accesses the perspectives manager 310 via the PACS system 300, for example. In an embodiment, RIS and PACS systems may be integrated into a single system, for example, with shared patient and exam contexts. Thus, the user access relevant prior history for a patient (e.g., images and reports). Using different perspectives 320, 330 the user has already created, the user may switch between perspectives 320, 330 to view desired information.

The medical perspectives 320, 330 may be delivered to the user in a variety of ways. For example, perspectives 320, 330 may be delivered via a preselected set of components and/or workflows from a medical software and/or hardware provider. Perspectives 320, 330 may also be delivered via perspectives created by a system administrator. Additionally, a user may dynamically create perspectives 320, 330 during operation of the system 300 (i.e., "on the fly"). Thus, the user may select images, components and/or applications for display in viewable areas of one or more monitors based on workflow. The information/configuration may then be saved in one or more perspectives 320, 330. The user may toggle between perspectives to read an exam or other data on a variety of devices such as displays and/or printers. The user may save perspectives, exams, reports, and/or other data via the manager 310.

In an embodiment, perspectives 320, 330 may use rules to filter information displayed in a perspective. Thus, a default perspective 320 may show all available images, but perspective 330 may be filtered to only show lateral images for a certain subject.

In an embodiment, system 300 may be integrated in a universal workstation providing a plurality of diagnostic viewing applications and other applications. The workstation may provide dozens of medical applications with hundreds of components and workflows, for example. Perspectives 320, 330 and perspectives manager 310 may be used to filter out images and/or application components that a user does not use in a routine workflow, for example.

Perspectives may be used to logically group different images and/or other data or applications. For example, perspectives may be defined for images, examination results, laboratory data, patient history data, structured report data, DICOM data, and/or other data or applications, for example. Rules, configuration options, and/or other criteria may be defined in order to define perspectives. In an embodiment, perspectives 320, 330 do not eliminate or change information but rather order information in a certain way. For example, information important to a user may be displayed first, with additional information available via different perspectives. In an embodiment, the manager 310 may "learn" through user selection or other configuration information, for example, to create perspectives automatically without manual intervention by the user. In an embodiment, the manager 310 may work together with a rules-based context manager to filter and display information.

In an embodiment, images in perspectives 320, 330 may be organized according to one or more criterion. For example, the default perspective 320 includes a first set of images organized according to a default criterion, while the second perspective 330 includes a second set of images organized according to a second criterion. The second criterion may be different from the default criterion, for example. Additionally, the second set of images may be a subset of the first or default set of images, which may include all available images for a subject, procedure, modality, and/or user, for example.

In an embodiment, the criterion includes image attributes, such as procedure-specific image attributes. For example, the second perspective 330 may be organized or laid out based on mammogram-specific image attributes found in image DICOM headers. Use of image attributes in determining a perspective layout allows precision in reproducing a perspective for each instance of a procedure, for example.

In an embodiment, the perspectives manager 310 includes one or more tools that may be used for navigation and/or manipulation of the images within a perspective 320, 300. Tools may include regular tools and/or directional tools, for example. Regular tools may include window width, window level, inversion, and/or zoom, for example. Directional tools may include pan and spatial cursor, for example. In an embodiment, when a regular tool is applied to an image, such as a left breast image, effects of the tool are also applied synchronously to a corresponding image, such as a right breast image. In an embodiment, when a directional tool is applied to an image, such as a left breast image, effects of the tool are mirrored on a corresponding image, such as a right breast image.

In an embodiment, the system 300 includes a report generator (not shown). The report generator may be part of the perspectives manager 310 or may be a separate system. The report generator allows image findings, image data, and/or other data to be integrated and stored and/or transmitted in a report. In an embodiment, the report generator includes one or more templates for report generation. A user may use the template(s) to record findings and other data in a report, for example. The template may include standardized and/or predefined results and data selectable by a user to generator a report, for example. The template may also accommodate free-form data, images and/or multimedia content for a report, for example.

In an embodiment, the perspectives manager 310 and perspectives 320, 330 are implemented as instructions on a computer-readable storage medium within the PACS system 300, such as a hard disk drive and processor in a PACS workstation. The perspectives manager 310 may be implemented as a perspectives management routine to coordinate images in one or more perspectives. The perspectives management routine allows a user to switch between perspectives to view different image layouts, for example. The instructions may also include a processing routine capable of processing images in the perspectives according to display functions, editing functions, and/or transmission functions, for example. For example the processing routine may facilitate printing of image(s) and/or report(s), editing image(s), and/or modifying a display of image(s). The set of instructions may further include a reporting routine for generating a report based on a template including analysis results relating to the perspectives. The set of instructions may also include a perspective creation routine for creating at least one perspective based on imaging-specific attributes.

Figure 4:
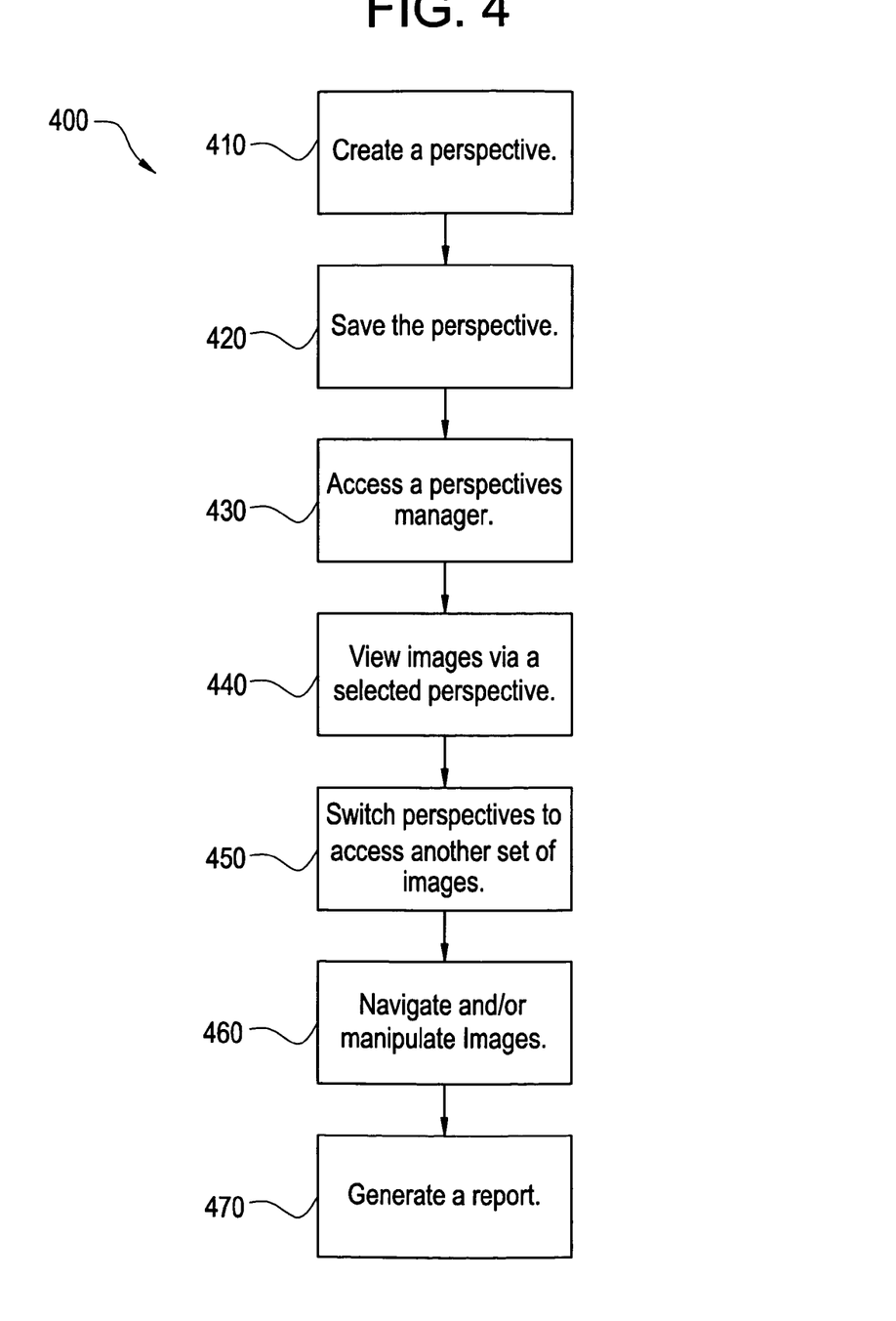
FIG. 4 illustrates a flow diagram for a method for managing multiple applications and workflows in accordance with an embodiment of the present invention.

FIG. 4 illustrates a flow diagram for a method 400 for managing multiple applications and workflows in accordance with an embodiment of the present invention. First, at step 410, a perspective is created. For example, a perspective may be created by a system administrator, by a user, and/or automatically by a software program. A perspective may capture and store workflow, images, applications, reports, and/or other information, for example. A perspective may be created for a particular user or group of users (e.g., surgeons, radiologists, cardiologists, etc.), for a particular use or group of uses (e.g., image-guided surgery, radiology reading (such as mammography or chest screening), structured reporting, examination, etc.), for a particular modality (e.g., computed tomography, digital radiography, digital x-ray, x-ray, ultrasound, magnetic resonance imaging, etc.), and/or for a particular platform (e.g., a PACS, an integrated RIS/PACS, an imaging system, etc.), for example.

Then, at step 420, the perspective is saved. The perspective may be saved in volatile and/or non-volatile storage, for example. In an embodiment, the perspective may be saved in association with a particular user, group of users, application, and/or platform, for example. The perspective saves visual component positioning and interactions based on workflow, for example.

Next, at step 430, a user accesses a medical perspectives manager, such as the manager 310. The user and/or software may select a perspective to open using the perspectives manager. In an embodiment, certain restrictions and/or permissions may limit which perspectives a particular user may access. In an embodiment, a user is authenticated (e.g., through a password, passcode, and/or biometric identification) at the manager. The manager then automatically authenticates the user at the relevant applications and/or systems associated with the selected perspective. Alternatively, authentication may be performed separate for each application and/or system access through the perspective. In an embodiment, a default perspective is automatically selected for a user.

At step 440, the user views one or more images via the selected perspective. The user may also utilize resources, such as applications, systems, workflows, and/or data, via the selected perspective. For example, the user views images, laboratory results, and patient histories through the selected perspective. The perspective allows information to be customized for the particular user. Then, at step 450, the user may switch between perspectives to access another set of images and/or resources, such as information, applications, and/or workflows. For example, the user may switch between a perspective showing all mammography images for a patient and a perspective showing only Cranio-Caudal view mammography images for the patient.

Next, at step 460, images may be navigated and/or manipulated in a perspective. For example, a user may zoom in on a particular area of one or more images. Additionally, for example, a user may adjust contrast in one or more images. In an embodiment, navigation and/or manipulation may occur manually through a user and/or automatically via software.

Then, at step 470, a report may be generated. In an embodiment, a structured report may be generated using templates and a standardized lexicon. For example, a user may select options within a template to document his or her findings regarding an image. A report may be generated by a user and/or by software analysis, for example.

In an embodiment, the method 400 may also include filtering information available in one or more perspectives based on rules, such as context-based rules. The rules may be used to further customize and/or organize information presented to a user based on one or more defined criteria, such as image attributes. Ordering and reducing information improves user workflow and increases productivity.

Thus, certain embodiments provide for improved screening analysis using medical perspectives. Certain embodiments increase productivity of a radiologist, cardiologist, or other user reviewing images by focusing a set of images for review. Certain embodiments help to optimize display and layout of a set of images within perspectives. Certain embodiments provide tools to analyze multiple images at a time with little physical effort. Certain embodiments allow electronic image review without sorting or hanging images manually.

Certain embodiments provide multiple perspectives allowing flexibility and adaptability to image and/or procedure characteristics. Use of image level information helps to ensure that each image is put in a desired position and is ready to make use of synchronized tools that reduce the overhead of reading images.

Certain embodiments allow workflow steps to be saved in the form of perspectives. The availability of multiple perspectives allows users to "program" a screening review, for example. A user may seamlessly toggle between perspectives to view different sets of images and other data and/or functions. In certain embodiments, a user may toggle between perspectives without touching a keyboard or mouse using a technique such as voice command and/or gaze tracking. Alternatively, a user may toggle between perspectives using a single click from a mousing device or a button. Thus, certain embodiments allow a user to view only the information he or she wants in the workflow he or she wants.

In certain embodiments, integrating perspectives and perspective management into a PACS workstation increases the efficiency of a user, such as a radiologist, because the PACS workstation has access to historical exams on an archive, rather than manual retrieval of historical exams on a standalone workstation. Additionally, comparison exams from other modalities may be accessed via a PACS workstations, rather than manual retrieval of comparison data on a standalone workstation. Furthermore, a RIS report may be generated and/or edited directly via a PACS workstation or on-board dictation system. An integrated RIS/PACS system may be provided rather than a standalone workstation required a third party dictation system and later transcription for incorporation into a RIS report. Certain embodiments also provide cost savings and flexibility benefits for exam reading, such as mammography or chest reading.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for using medical perspectives for improved screening analysis, said system comprising:
 a picture archiving and communication system (PACS) workstation capable of being used for reviewing images;
 at least one display capable of displaying images for review;
 a perspectives manager to facilitate dynamic switching by a user among a plurality of perspectives and to facilitate dynamic user modification of at least one of the plurality of perspectives, the plurality of perspectives including:
 a default perspective including a first plurality of images organized according to a default criterion for display in a first perspective layout to optimize display of the first plurality of images within the default perspective, wherein said default perspective saves visual component positioning and interaction between said first plurality of images based on workflow and is used to review said first plurality of images via said PACS workstation; and
 a second perspective including a second plurality of images organized according to a second criterion, wherein said second perspective is selectable by a user and wherein said second perspective saves visual component positioning and interaction between said second plurality of images based on workflow and is used to review said second plurality of images via said PACS workstation, wherein said perspectives manager provides context sharing among images and applications in at least one of the plurality of perspectives at said PACS workstation and wherein said perspectives manager matches images in each perspective to areas of each perspective layout based on image information associated with the images to allow the perspective to be reproduced for each instance of a procedure, said perspectives manager automatically selecting the default perspective for the user based on information related to the user.

2. The system of claim 1, wherein said second plurality of images comprises a subset of said first plurality of images.

3. The system of claim 1, wherein said default criterion allows display of all available images.

4. The system of claim 1, where said second criterion includes image attributes.

5. The system of claim 4, wherein said image attributes include procedure-specific image attributes.

6. The system of claim 4, wherein said second perspective includes a layout of said second plurality of images based on said image attributes.

7. The system of claim 1, further comprising at least one tool for at least one of navigation and manipulation of images.

8. The system of claim 7, wherein said at least one tool allows a user to at least one of navigate and manipulate one or more of said images in a synchronous manner within a perspective.

9. The system of claim 1, further comprising a template for recording findings to generate a report.

10. The system of claim 9, wherein said template includes a plurality of screening results selectable by a user.

11. A computer-implemented method for providing medical perspectives for improved screening analysis, the method comprising:
 providing a default perspective for reviewing images on a picture archiving and communication system (PACS) workstation, wherein said default perspective includes a first plurality of images organized according to a default criterion for display in a first perspective layout to optimize display of the first plurality of images within the default perspective, wherein said default perspective saves visual component positioning and interaction between said first plurality of images based on workflow; and
 allowing a user to switch among a plurality of perspectives via a perspectives manager by dynamically selecting a second perspective for reviewing images on said PACS workstations, wherein said second perspective includes a second plurality of images organized according to a second criterion, said second perspective saving visual component positioning and interaction between said second plurality of images based on workflow, wherein the perspective manager facilitates dynamic user modification of at least one of the plurality of perspectives, and wherein said perspectives manager provides context sharing among images and applications in at least one of the plurality of perspectives, said perspectives manager matching images in each perspective to areas of each perspective layout based on image information associated with the images to allow the perspective to be reproduced for each instance of a procedure, said perspectives manager automatically selecting the default perspective for the user based on information related to the user.

12. The method of claim 11, wherein said default criterion allows display of all available images.

13. The method of claim 11, where said second criterion includes image attributes.

14. The method of claim 13, wherein said image attributes include procedure-specific image attributes.

15. The method of claim 11, further comprising at least one of navigating and manipulating images in at least one of said first and said second plurality of images.

16. The method of claim 15, wherein said at least one of navigating and manipulating said images comprises at least one of navigating and manipulating one or more of said images in a synchronous manner within a perspective.

17. The method of claim 11, further comprising generating a report using a plurality of screening results selectable by a user.

18. A system for image analysis using perspectives, said system comprising:
 a perspectives manager to facilitate dynamic switching by a user among a plurality of perspectives and to facilitate dynamic user modification of at least one of the plurality of perspectives, the plurality of perspectives including:
 a default perspective including a first plurality of images organized according to a default criterion for display in a first perspective layout to optimize display of the first plurality of images within the default perspective, wherein said default perspective saves visual component positioning and interaction between said first plurality of images based on workflow and is used to review said first plurality of images via a picture archiving and communication system (PACS) workstation; and a second perspective including a second plurality of images organized according to a second criterion, wherein said second perspective is selectable by a user and wherein said second perspective saves visual component positioning and interaction between said second plurality of images based on workflow and is used to review said second plurality of images via said PACS workstation, wherein said second plurality of images comprises a subset of said first plurality of images, wherein said second criterion comprises image attributes, wherein said perspectives manager provides context sharing among images and applications in at least one of the plurality of perspectives at said PACS workstation and wherein said perspectives manager matches images in each perspective to areas of each perspective layout based on image information associated with the images to allow the perspective to be reproduced for each instance of a procedure.

19. An article of manufacture comprising:

a non-transitory computer-readable storage medium; and executable program instructions embodied in the non-transitory computer readable storage medium that when executed by a programmable system cause the system to perform functions that implement a medical perspectives system, the functions comprising:

a perspectives management routine for coordinating a plurality of perspectives including images, wherein each of said plurality of perspectives saves visual component positioning and interaction between a group of images based on workflow, wherein said perspectives management routine allows a user to dynamically switch between perspectives to view different image layouts and to dynamically modify at least one of the plurality of perspectives; and a processing routine for processing images in said perspectives according to at least one of display functions, editing functions, and transmission functions, wherein said perspectives management routine provides context sharing among images and applications in at least one of the plurality of perspectives and wherein said perspectives manager matches images in each perspective to areas of each perspective layout based on image information associated with the images to allow the perspective to be reproduced for each instance of a procedure, said perspectives manager automatically selecting the default perspective for the user based on information related to the user.

20. The article of manufacture of claim 19, further comprising a reporting routine for generating a report based on a template including analysis results relating to said perspectives.

21. The article of manufacture of claim 19, further comprising a perspective creation routine for creating at least one perspective based on imaging-specific attributes.

* * * * *

UNITED STATES PATENT AND TRADEMARK OFFICE
CERTIFICATE OF CORRECTION

| | | |
|---|---|---|
| PATENT NO. | : 7,834,891 B2 | Page 1 of 1 |
| APPLICATION NO. | : 10/996631 | |
| DATED | : November 16, 2010 | |
| INVENTOR(S) | : Yarger et al. | |

It is certified that error appears in the above-identified patent and that said Letters Patent is hereby corrected as shown below:

Column 6, Line 52, delete "perspective 300." and insert -- perspective 320. --, therefor.

Column 8, Line 50, delete "perspective 320, 300." and insert -- perspectives 320, 330. --, therefor.

Column 11, Line 59, in Claim 4, delete "where" and insert -- wherein --, therefor.

Column 12, Line 43, in Claim 13, delete "where" and insert -- wherein --, therefor.

Column 13, Line 27, in Claim 19, delete "computer readable" and insert -- computer-readable --, therefor.

Signed and Sealed this
Thirty-first Day of January, 2012

David J. Kappos
*Director of the United States Patent and Trademark Office*